(12) United States Patent
Patel

(10) Patent No.: US 9,844,261 B2
(45) Date of Patent: Dec. 19, 2017

(54) MEDICATION REMINDER TOOTHBRUSH

(71) Applicant: Ashlesha Patel, Northbrook, IL (US)

(72) Inventor: Ashlesha Patel, Northbrook, IL (US)

(73) Assignee: Ashlesha A. Patel, Northbrook, IL (US)

( * ) Notice: Subject to any disclaimer, the term of this patent is extended or adjusted under 35 U.S.C. 154(b) by 0 days.

(21) Appl. No.: 14/857,426

(22) Filed: Sep. 17, 2015

(65) Prior Publication Data

US 2017/0079422 A1    Mar. 23, 2017

(51) Int. Cl.
| | |
|---|---|
| *A46B 9/04* | (2006.01) |
| *A46B 15/00* | (2006.01) |
| *A46B 17/04* | (2006.01) |
| *A61C 15/04* | (2006.01) |
| *A61J 7/04* | (2006.01) |

(52) U.S. Cl.
CPC ............ *A46B 15/0061* (2013.01); *A46B 9/04* (2013.01); *A46B 17/04* (2013.01); *A61C 15/043* (2013.01); *A61J 7/04* (2013.01); *A46B 2200/1066* (2013.01)

(58) Field of Classification Search
CPC ........ A46B 2200/1066; A46B 15/0055; A46B 15/0085; A46B 15/0091; A46B 15/0061; A46B 15/0069; A46B 15/0071; A46B 15/0073
USPC ...... 15/106, 167.1, 176.1, 247; 206/533–534
See application file for complete search history.

(56) References Cited

U.S. PATENT DOCUMENTS

| | | | |
|---|---|---|---|
| 3,561,592 A * | 2/1971 | McCool ............. | B65D 83/0454 206/533 |
| 3,738,480 A | 6/1973 | Chesley | |
| 4,140,140 A | 2/1979 | Proia et al. | |
| 4,821,752 A * | 4/1989 | Widlak ................ | A46B 5/0095 132/309 |
| D361,209 S * | 8/1995 | Curtis ............................ | D4/104 |
| 5,608,940 A | 3/1997 | Panyon, Jr. et al. | |
| 5,924,567 A * | 7/1999 | Wenum .................. | A46B 17/04 206/15.3 |
| 5,950,641 A * | 9/1999 | Taveras .................. | A46B 7/046 132/309 |
| 6,053,338 A * | 4/2000 | Avery ................ | A46B 15/0055 211/184 |
| 6,129,241 A | 10/2000 | Rai | |
| 8,857,617 B2 * | 10/2014 | Balakier ................... | A61J 7/04 206/528 |
| 2002/0121283 A1 | 9/2002 | Piccolo et al. | |
| 2005/0011803 A1 * | 1/2005 | Chafoulias ......... | B65D 83/0481 206/528 |

(Continued)

FOREIGN PATENT DOCUMENTS

FR    1563086    *    4/1969    ............ A46B 15/00

OTHER PUBLICATIONS

International Search Report for related PCT Application No. PCT/US2016/051321 reported on Dec. 23, 2016.

*Primary Examiner* — Laura C Guidotti

(74) *Attorney, Agent, or Firm* — Miller, Matthias & Hull LLP

(57) ABSTRACT

A medical device has a receptacle and a toothbrush. The receptacle has a container and a closure. The container has an open end and a closed end. The toothbrush has a stalk and bristles. The stalk is operatively associated with the closed end and the bristles. The closure selectively closes the open end.

17 Claims, 8 Drawing Sheets

(56) References Cited

U.S. PATENT DOCUMENTS

2012/0325688 A1\* 12/2012 Davis ................ A46B 15/0055
206/38

\* cited by examiner

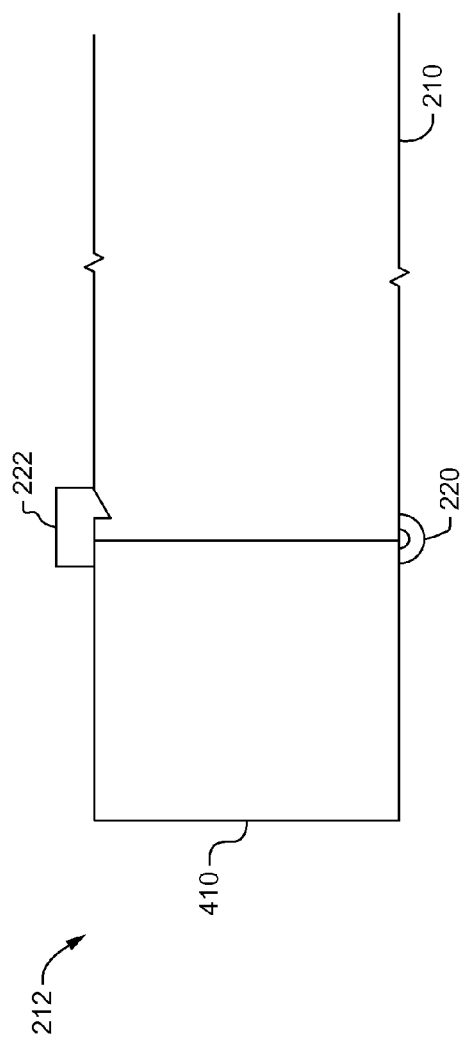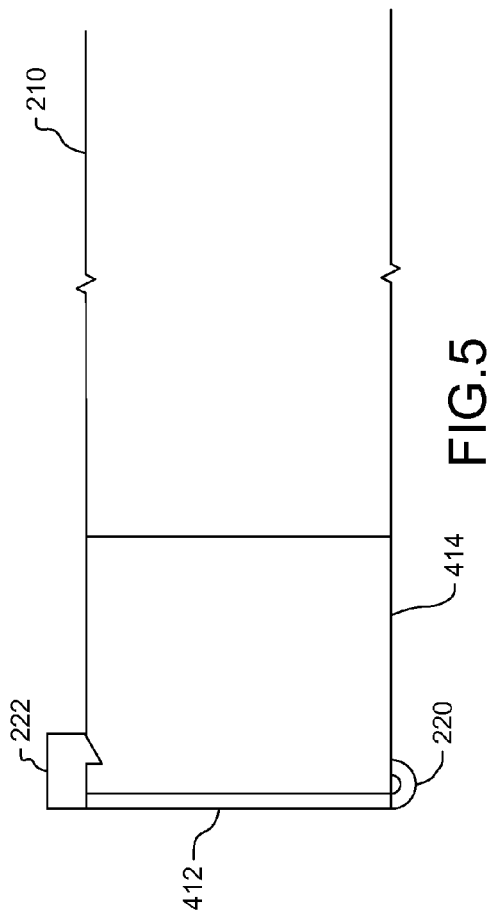

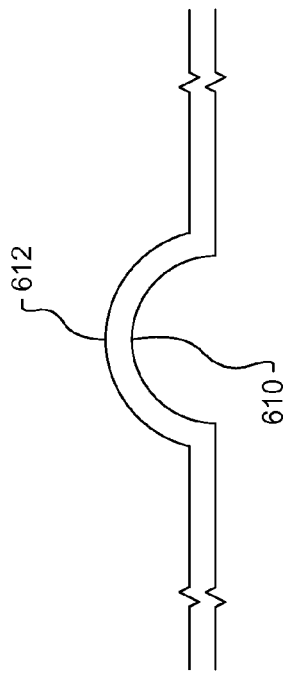
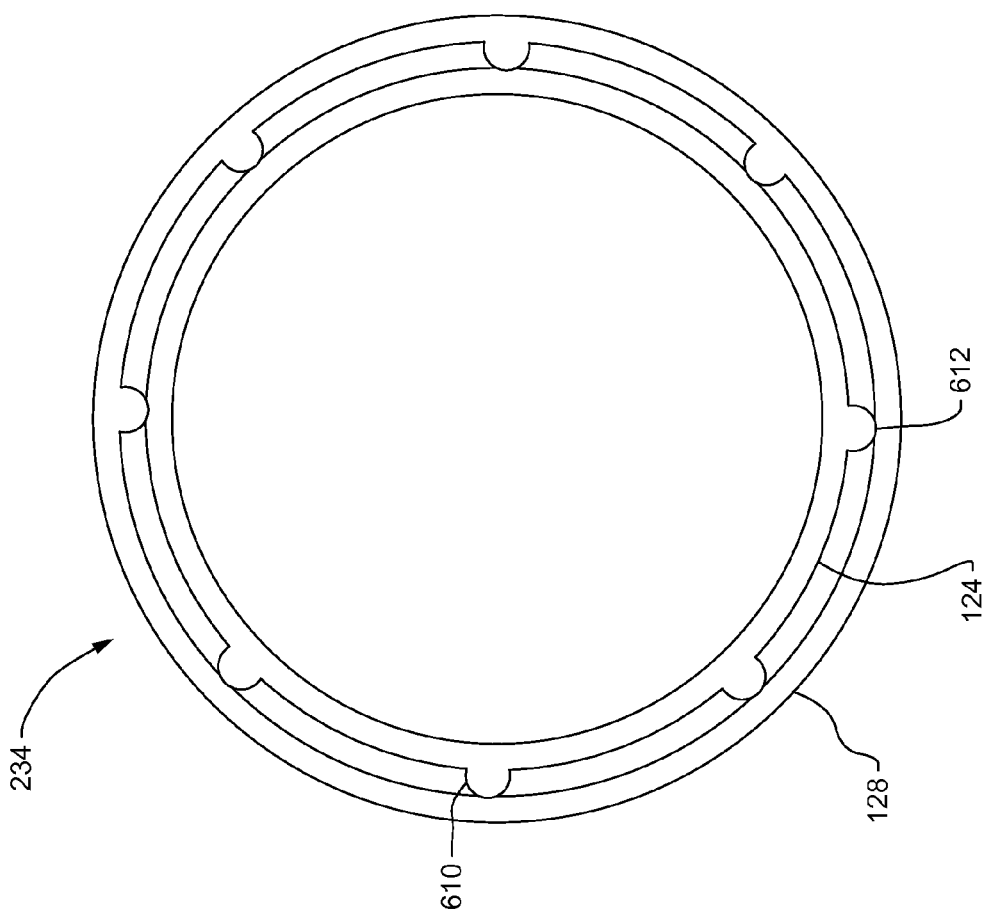

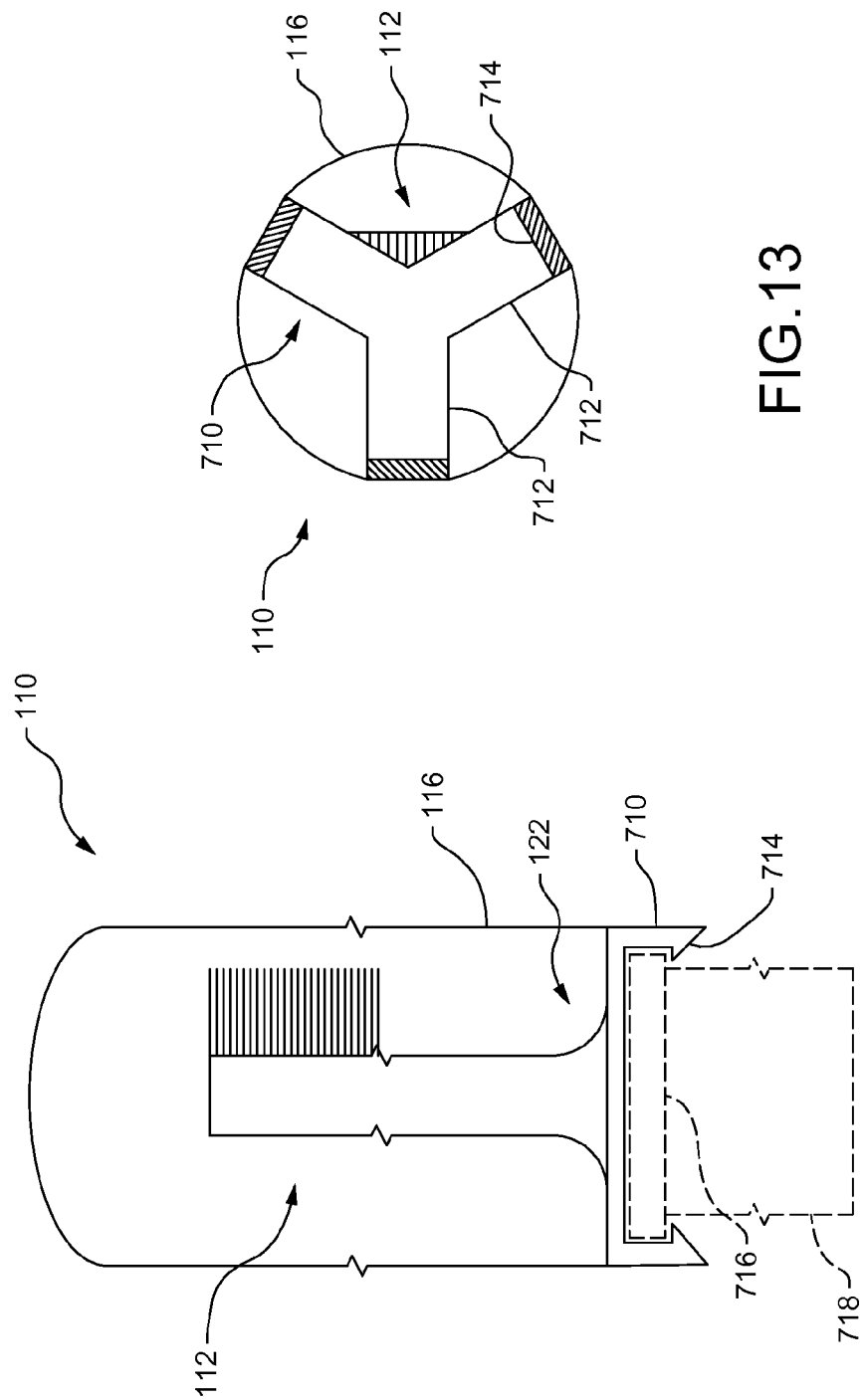

MEDICATION REMINDER TOOTHBRUSH

FIELD OF THE DISCLOSURE

The present disclosure relates generally to health products and, more particularly, to dental hygiene products and medication containers.

BACKGROUND OF THE DISCLOSURE

Healthcare professionals may prescribe medications to patients which are often to be taken according to a schedule. For example, a doctor may prescribe a medication that the patient is to take once daily. Typically, medications come in tablet form and are packaged in capped bottles to which a label is affixed. The label usually includes the patient's name, the name of the medication, the medication dosage, instructions for taking the medication, and side effects that the patient may experience.

After the patient has been prescribed the medication, it is the patient's responsibility to follow the medication's instructions and to take the medication on schedule. However, patients often fail to correctly take the medication prescribed to them, if at all. For instance, a patient may not regularly take medication and may forget the prescription because it is outside the patient's usual routine. In other instances, a patient may take multiple medications and may become confused as to which medication to take at a certain time. In other cases, a patient may be unsure whether he or she took the medication and has since forgotten. In any of these situations, the failure to take a medication according to instructions and on schedule may have adverse health effects on the patient.

Systems and methods of providing containers to sort and remind patients of their medications are available. Such containers are often arranged with compartments for each day of the week in which medication is stored. More specifically, patients sort their medications at the beginning of the week into these compartments and take the medication or medications in each individual compartment as the week progresses. However, even with these medication sorting containers, patients still sometimes fail to take their medications on time.

Existing strategies for reminding patients to take their medications are well shown by Jackson in U.S. Pat. No. 3,738,480 (hereinafter the '480 patent). The '480 patent discloses a series of compartments in a body, with each compartment labeled for a specific time.

Improvements in medication storage containers are desired to merge medication taking into patients' already existing customary routines and thereby help patients remember to timely take their medications. Furthermore, patients who take their medications on time may heal more quickly or better manage their ongoing conditions, reducing their needs to repeatedly visit their physicians and thereby reducing overall healthcare costs.

SUMMARY OF THE DISCLOSURE

In accordance with one embodiment, a medical device is disclosed. The medical device may include a receptacle and a toothbrush. The receptacle may have a container and a closure. The container may have an open end and a closed end. The closure may selectively close the open end. The toothbrush may have a stalk operatively associated with the closed end and bristles operatively associated with the stalk.

In accordance with another embodiment, a medical device is disclosed. The medical device may include a base and a toothbrush. The base may be adapted to operatively associate with a medication bottle. The toothbrush may have a stalk operatively associated with the base and bristles operatively associated with the stalk.

In accordance with yet another embodiment, a method for reminding a patient to take medication is disclosed. The method may include providing a toothbrush operatively associated with a selectively closeable container. The method may also include filling the container with medication. The method may further include using the toothbrush in a regular dental hygiene routine. The method may yet further include taking the medication during the routine.

In accordance with a further embodiment, a method for reminding a patient to take medication is disclosed. The method may include providing a toothbrush operatively associated with a base adapted to connect with a medication bottle. The method may further include connecting the base with the medication bottle. The method may also include using the toothbrush in a regular dental hygiene routine. The method may yet further include taking the medication during the routine.

These and other aspects and features will become more readily apparent upon reading the following detailed description when taken in conjunction with the accompanying drawings. In addition, although various features are disclosed in relation to specific exemplary embodiments, it is understood that the various features may be combined with each other, or used alone, with any of the various exemplary embodiments without departing from the scope of the disclosure.

BRIEF DESCRIPTION OF THE DRAWINGS

FIG. 4 is a cross-sectional view of the embodiment of FIG. 2 taken along line Y-Y.

FIG. 5 is a cross-sectional view of the embodiment of FIG. 3 taken along line W-W.

FIG. 10 is a cross-sectional view of the embodiment of FIG. 2 taken along line X-X.

FIG. 11 is a detail view of FIG. 10.

FIG. 12 is a side view of a medical device, in accordance with an even further embodiment of the present disclosure.

FIG. 13 is an end view of the embodiment of FIG. 12.

While the present disclosure is susceptible to various modifications and alternative constructions, certain illustrative embodiments thereof will be shown and described below in detail. The disclosure is not limited to the specific embodiments disclosed, but instead includes all modifications, alternative constructions, and equivalents thereof.

DETAILED DESCRIPTION

Figure 1:
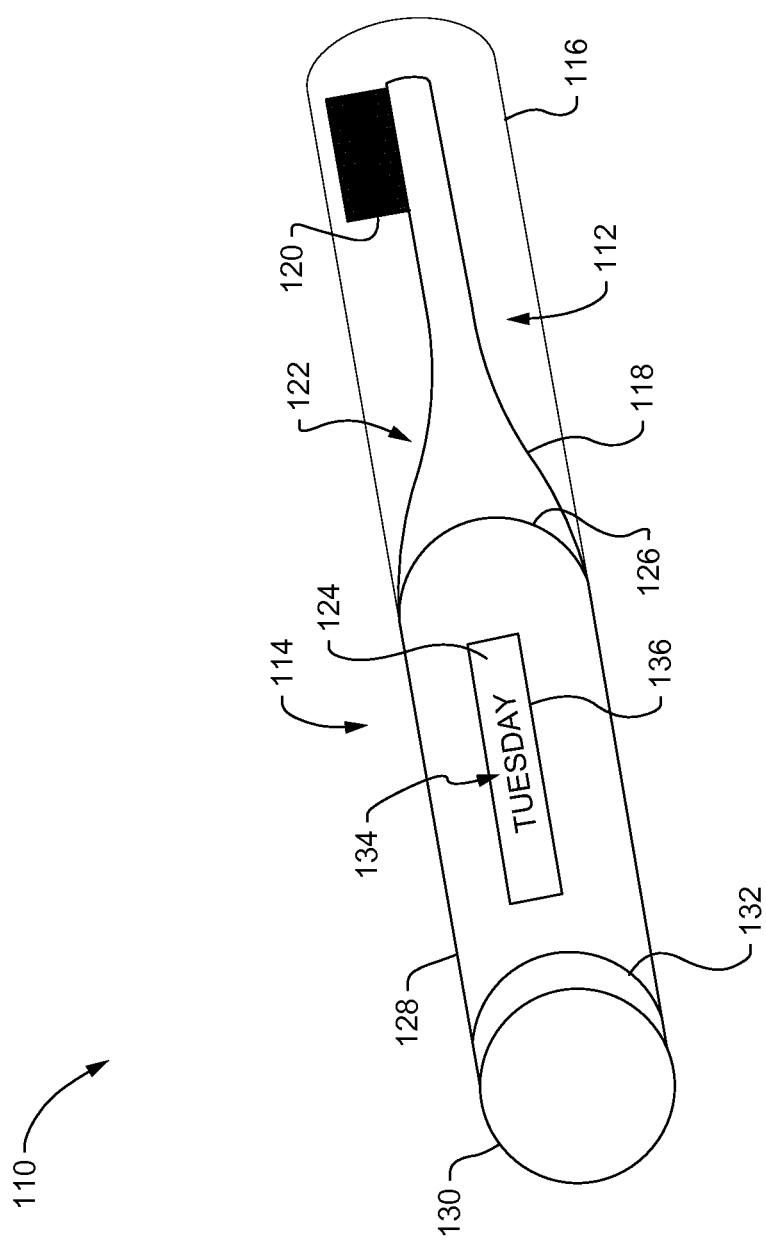
FIG. 1 is a perspective view of a medical device, in accordance with one embodiment of the present disclosure.

Referring now to the drawings and with specific reference to FIG. 1, a medical device consistent with certain embodiments of the present disclosure is generally referred to by reference numeral 110. As used herein, the term "medical device" refers to a tool that performs a manual operation involving dental hygiene and medication storage associated with a particular industry, such as, but not limited to, dentistry, pharmacy, medicine, etc. It is to be understood that the medical device 110 is shown primarily for illustrative purposes to assist in disclosing features of various embodiments, and that FIG. 1 does not depict all of the components of a medical device 110.

The medical device 110 may include a toothbrush 112, a receptacle 114, and a shell 116. To protect the toothbrush 112 when the medical device 110 is not in use, the receptacle 114 may be selectively operatively associated with the shell 116. The toothbrush 112 may include a stalk 118 and bristles 120 operatively associated with the stalk 118. In some embodiments, the stalk 118 may have a conical transition region 122. The stalk 118 may be further operatively associated with the receptacle 114.

More specifically, the receptacle 114 may include a container 124 that may have a closed end 126 with which the stalk 118 may be operatively associated. In addition to the container 124, the receptacle 114 may further include a cover 128 and a closure 130, as shown best in FIG. 2. Besides the closed end 126, the container 124 may also have an open end 132 and at least one indicium 134. It should be understood that the indicia 134 may be raised, lowered, or flush with the container 124 and may be marked by any method known in the art, including, but not limited to, printing, embossing, engraving, stamping, molding, etc. The cover 128 may at least partially surround the container 124 and may include a window 136 through which the indicia 134 may be visible. To close the container 124, it may be selectively operatively associated with the closure 130 at the open end 132. It should be understood that the closure 130 may be operatively associated with the container 124 by any method known in the art such as, but not limited to, screw threads, snap fittings, press fittings, hinges, catches, clips, etc. In some embodiments, the closure 130 may be integral with the cover 128, as illustrated in FIG. 2 and described below.

Figure 2:
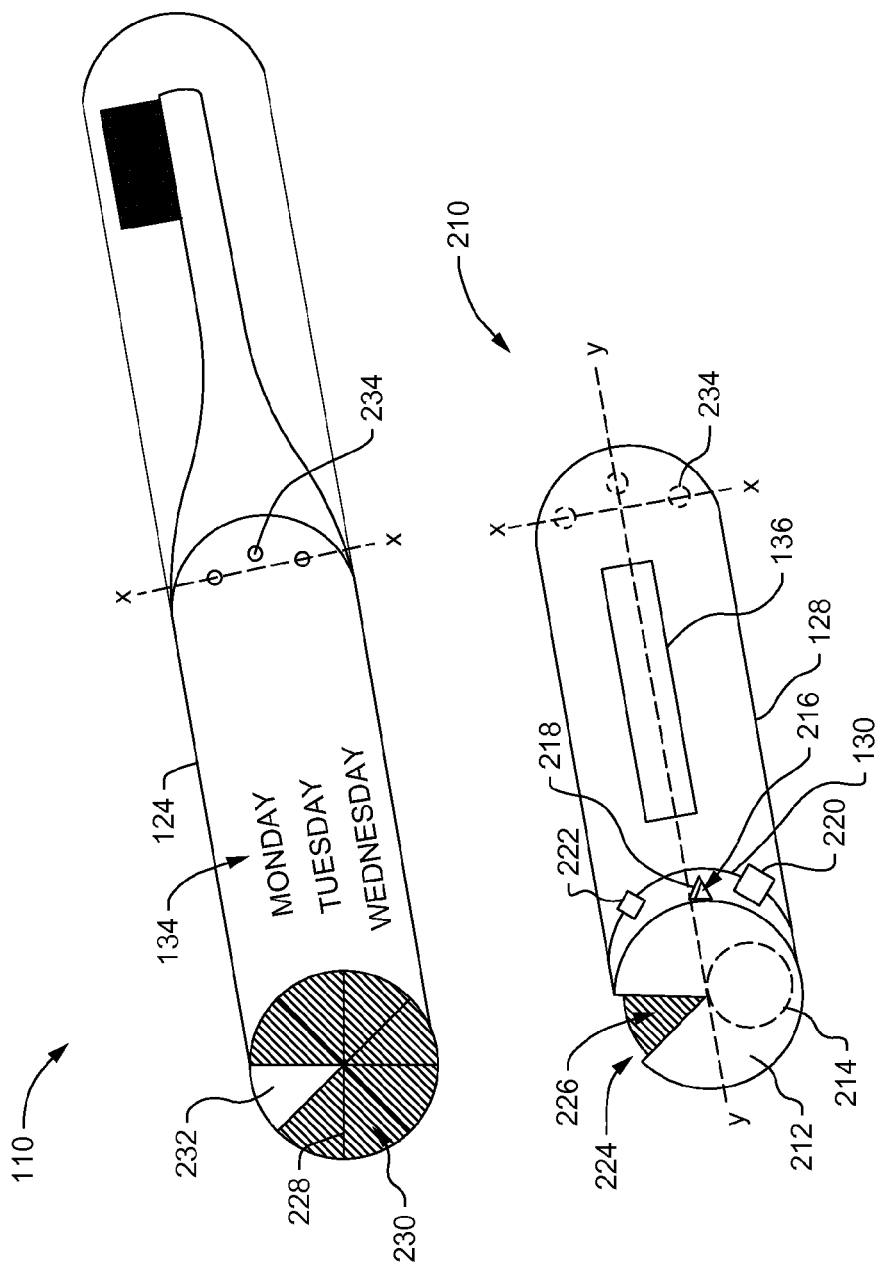
FIG. 2 is an exploded perspective view of the medical device, in accordance with another embodiment of the present disclosure.

Referring to FIG. 2, the closure 130 and the cover 128 may be one piece forming a sheath 210. In one embodiment, the sheath 210 may include a chamber 212 for storing medical or hygienic supplies, such as, but not limited to a spool of dental floss 214. The chamber 212 may include an outlet 216 that may have a cutter 218 for cutting dental floss from the spool 214 in such an embodiment.

In other embodiments, the chamber 212 may be operatively associated with the sheath 210 via a hinge 220. In further embodiments, the chamber 212 may be selectively held closed by a barbed clasp 222, as will be described below and shown in FIGS. 4 and 5. In other embodiments, the chamber 212 may be configured to have a cutout 224 and the sheath 210 may be configured to have an opening 226.

The cutout 224 and the opening 226 may work together to selectively provide access to the container 124. The cutout 224 and the opening 226 are more specifically shown in FIGS. 8 and 9 and will be described below.

Focusing on the container 124, it may be rotatably associated with the sheath 210 and may further include longitudinal dividers 228 that work together to form compartments 230. At least two of the longitudinal dividers 228 may be joined by a wall 232, closing one of the compartments 230. As the sheath 210 is rotated about the container 124, the opening 226 and the cutout 224 may selectively provide access to individual compartments 230 and the indicia 134 may be successively visible through the window 136. Rotating the sheath 210 may also selectively close the container 124 when the opening 226 is overshadowed by the wall 232. In some embodiments, to aid in selecting a specific compartment 230 or securely closing the container 124, the container 124 and the sheath 210 may be equipped with corresponding indexing structures 234 which are further shown in FIG. 10 and will be described below. In other embodiments, selectively accessing a specific compartment 230 or selectively closing the container 124 may be aided by configuring the container 124 and the sheath 210 to have polygonal cross-sections as illustrated in FIG. 3.

Figure 3:
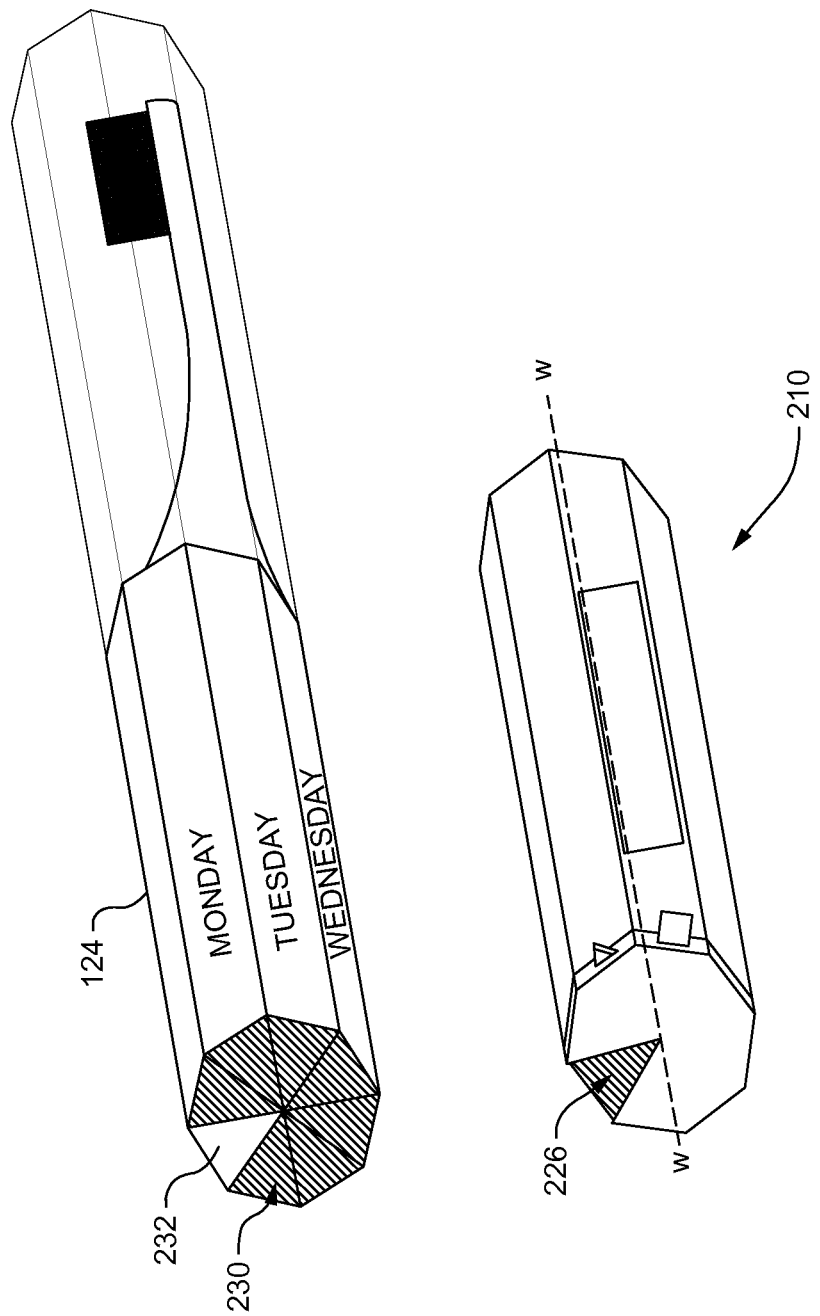
FIG. 3 is an exploded perspective view of the medical device, in accordance with a further embodiment of the present disclosure.

As shown in FIG. 3, the container 124 and the sheath 210 may be cross-sectionally polygonal. For example, to provide seven open compartments 230 (one for each day of the week) and one compartment 230 closed by wall 232 for overshadowing the opening 226 to selectively close the container 124, the container 124 and the sheath 210 may be octagonal. It should be understood, however, that the container 124 and the sheath 210 may be cross-sectionally configured as any polygon. In these polygonal embodiments, the sheath 210 may be slidably and removably associated with the container 124. To selectively access the individual compartments 230 or to close the container 124, the sheath 210 may be removed, rotationally repositioned with respect to the container 124, and remounted on the container 124. Put another way, by removing, rotating, and remounting the sheath 210, the opening 226 may selectively provide access to the individual compartments 230 or be overshadowed by the wall 232.

Turning now to FIG. 4, mentioned above, the chamber 212 may be configured as a cap 410 operatively associated with the sheath 210 via the hinge 220 and secured to the sheath 210 with the barbed clasp 222. In another embodiment, as shown in FIG. 5, the chamber 212 may be configured as a flap 412 operatively associated with a well 414 formed in the sheath 210 via the hinge 220 and secured to the sheath 210 by the barbed clasp 222. These embodiments are further shown in FIGS. 6-9 and more specifically described below.

Figure 8:
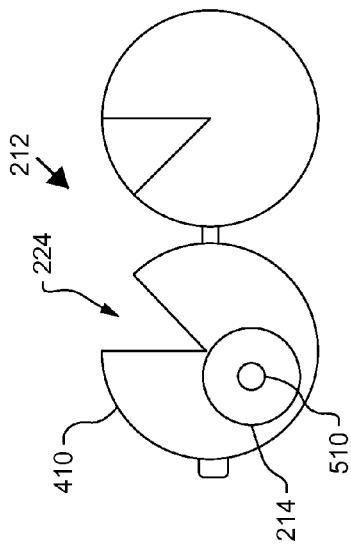
FIG. 8 is an exploded end view of the embodiment of FIG. 2.
Figure 6:
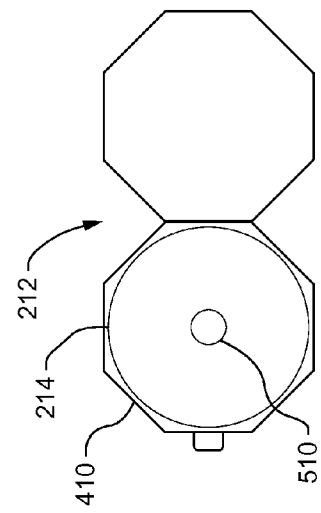
FIG. 6 is an exploded end view of the medical device, in accordance with a yet further embodiment of the present disclosure.
Figure 9:
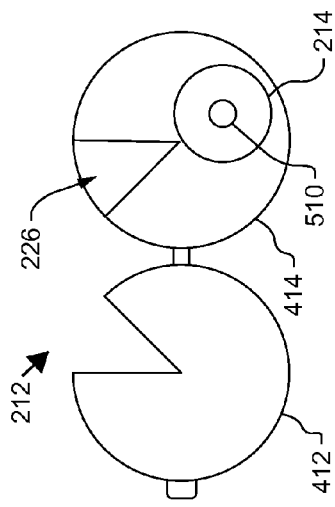
FIG. 9 is an exploded end view of the medical device, in accordance with a still further embodiment of the present disclosure.
Figure 7:
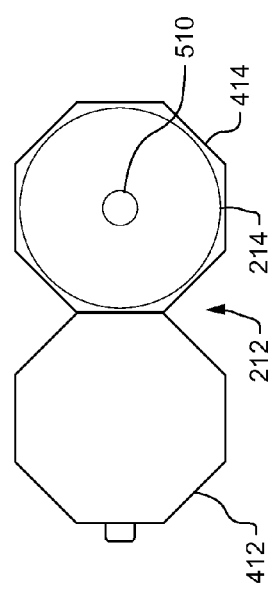
FIG. 7 is an exploded end view of the medical device, in accordance with an additional embodiment of the present disclosure.

Referring now to FIG. 6, in some embodiments, the spool of dental floss 214 contained in the chamber 212 may be mounted to the cap 410 via a post 510. In other embodiments, as shown in FIG. 7, the spool of dental floss 214 may be mounted to the well 414 via the post 510. It should be appreciated that, in some embodiments, as shown in FIG. 8, the spool of dental floss 214 and the post 510 may be offset in the cap 410 to accommodate the cutout 224. It should also be appreciated that, in other embodiments, as shown in FIG. 9, the spool of dental floss 214 and the post 510 may be offset in the well 414 to accommodate the opening 226.

Looking now at FIG. 10 and returning to the indexing structures 234 previously mentioned in the description of FIG. 2, in some embodiments, the container 124 may further include bumps 610 and the cover 128 may include divots 612. In other embodiments, the container 124 may have divots 612 and the cover 128 may have bumps 610. As detailed in FIG. 11, the bumps 610 and divots 612 may be configured so that the bumps 610 fit into but easily slide out of the divots 612 to aid in selectively rotating or indexing the cover 128 about the container 124. In this manner, the indexing structures 234 may be tactilely perceived as the bumps 610 fit into and slide out of divots 612.

Moving on to FIGS. 12 and 13, in a different embodiment, the medical device 110 may include a base 710, the toothbrush 112, and the shell 116. The toothbrush 112 may be of any preferential length and may be operatively associated with the base 710. As above, in some embodiments, the toothbrush 112 may include the conical transition region 122. The shell 116 may be removably associated with the base 710 and may envelop the toothbrush 112 to protect the toothbrush 112 when the medical device 110 is not in use.

More specifically, in some embodiments, the base 710 may include arms 712 and barbs 714. The arms 712 may extend radially with respect to the toothbrush 112 and may be operatively associated with the barbs 714. The barbs 714 may be arranged to be perpendicular to the arms 712, to extend away from the toothbrush 112, and to face each other. Additionally, the barbs 714 may be adapted to snap onto a lid 716 of a standard medication bottle 718 commonly received by patients when filling medication prescriptions. It should be understood that the base 710 may have a different number of arms 712 than that shown in FIG. 13. It also should be understood that the base 710 may be configured differently in other embodiments, as illustrated in FIGS. 14 and 15.

Figure 15:
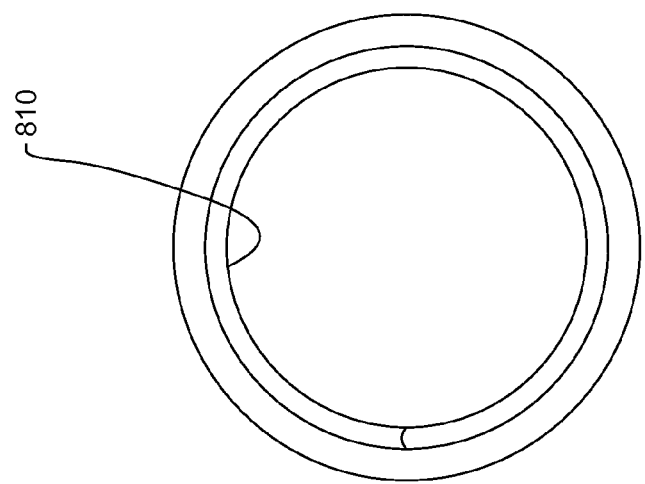
FIG. 15 is an end view of the embodiment of FIG. 14.
Figure 14:
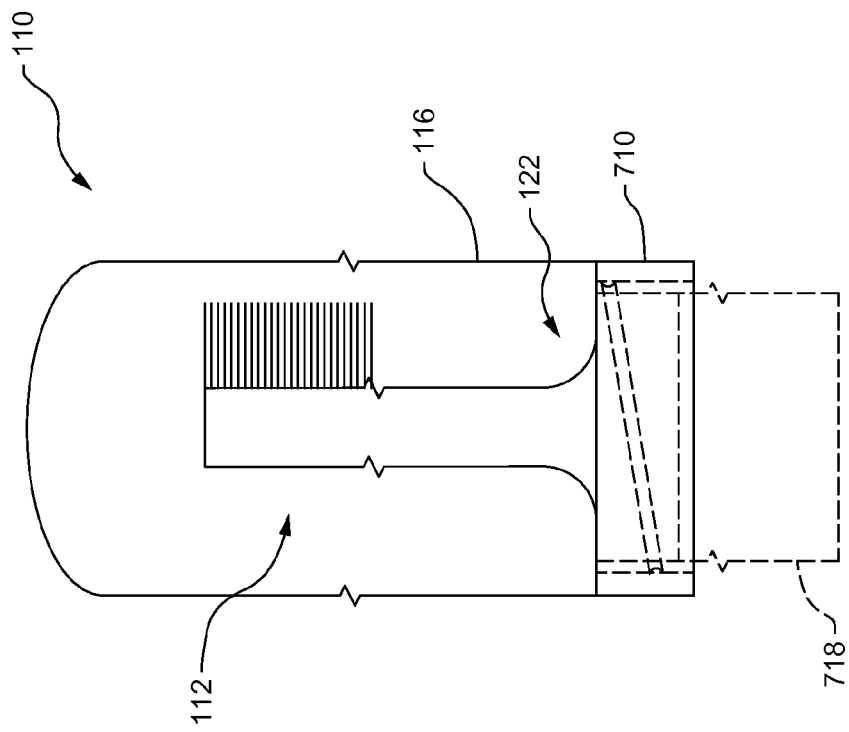
FIG. 14 is a side view of a medical device, in accordance with a still even further embodiment of the present disclosure.

Referring to FIGS. 14 and 15, the medical device 110 may include the toothbrush 112, the base 710, and the shell 116. As above, the toothbrush 112 may have the conical transition region 122, may be of any preferential length, and may be operatively associated with the base 710. Also as above, the shell 116 may be removably associated with the base 710. In some embodiments, as best shown in FIG. 15, the base 710 may include an internal thread 810 to threadably associate the base 710 with the standard medication bottle 718.

INDUSTRIAL APPLICABILITY

In general, the foregoing disclosure finds utility in various healthcare applications, such as, but not limited to, dental hygiene, internal medicine, pharmacy, and nutrition. In particular, the disclosed medical device may be used by patients who take medication and/or users who take dietary supplements in pill or tablet form. By using the disclosed medical device users may incorporate taking medication and/or dietary supplements into their usual tooth brushing routine. Furthermore, because tooth brushing is commonly a daily activity, users will be reminded at least daily to take their medications. Moreover, users' adherence to their medications' instructions may help users to heal more quickly, better manage their ongoing conditions, and prevent acute illness. The disclosed medical device may thus provide improvements to health and cost saving measures.

While the foregoing detailed description has been given and provided with respect to certain specific embodiments, it is to be understood that the scope of the disclosure should not be limited to such embodiments, but that the same are provided simply for enablement and best mode purposes. The breadth and spirit of the present disclosure is broader than the embodiments specifically disclosed and encompassed within the claims appended hereto. Moreover, while some features are described in conjunction with certain specific embodiments, these features are not limited to use with only the embodiment with which they are described, but instead may be used together with or separate from, other features disclosed in conjunction with alternate embodiments.

What is claimed is:

1. A medical device comprising:
   a container having an open end and a closed end;
   a closure selectively closing the open end;
   a cover adapted to fit about the container, the cover being rotatably associated with the container about an axis, the cover including a window such that indicia on the container are selectively visible through the window;
   corresponding indexing structures on the container and the cover, the indexing structures facing inwardly from an interior wall of the cover and the indexing structures facing outwardly from the container; and
   a toothbrush having a stalk operatively associated with the closed end and bristles extending from the stalk.

2. The device of claim 1, further comprising a shell enveloping the toothbrush.

3. The device of claim 1, wherein the closure is rotatably associated with the container.

4. The device of claim 3, wherein the closure includes a cutout, the cutout selectively closing the open end.

5. The device of claim 1, wherein the indexing structures on the container are divots, the indexing structures on the cover are bumps, and the humps fit into the divots.

6. The device of claim 1, wherein the indexing structures on the container are bumps, the indexing structures on the cover are divots, and the bumps fit into the divots.

7. The device of claim 1, wherein the closure is integral with the cover to form a sheath.

8. The device of claim 7, further comprising:
   a plurality of compartments inside the container formed by longitudinal dividers; and
   a wall formed between at least two of the longitudinal dividers, closing at least one of the compartments.

9. The device of claim 8, wherein the sheath includes an opening selectively overshadowed by the wall.

10. The device of claim 8, wherein the sheath is octagonal in cross-section and slidably and removably associated with the container and wherein an opening is provided in the sheath, the opening being selectively overshadowed by the wall.

11. The device of claim 1, further comprising:
    a chamber having an outlet, the chamber being operatively associated with the closure; and
    a supply of dental floss enclosed in the chamber.

12. The device of claim 11, further comprising a floss cutter in the outlet.

13. A medical apparatus, comprising:
    a medication bottle including a lid and a container;
    a base adapted to operatively associate with a medication bottle, wherein the base has a plurality of arms, each arm being operatively associated with and substantially perpendicular to a barb, the arms extending radially away from the toothbrush, the barbs facing radially inward towards each other, the barbs extending away from the toothbrush, and the barbs being adapted to snap onto the lid of the medication bottle; and
    a toothbrush having a stalk operatively associated with the base and bristles extending from the stalk, the stalk associated to the base opposite the medication bottle.

14. The apparatus of claim 13, wherein the base has an internal thread.

15. The apparatus of claim 13, further comprising a shell removably associated with the base and enveloping the toothbrush.

16. A method for reminding a patient to take medication, comprising:

providing a toothbrush, the toothbrush including a container having an open end and a closed end, a stalk operatively associated with the closed end and bristles extending from the stalk, a closure selectively closing the open end, a plurality of compartments inside the container formed by longitudinal dividers, a wall formed between at least two of the longitudinal dividers, closing at least one of the compartments, the toothbrush further including a cover adapted to fit about the container, the cover being rotatably associated with the container about an axis, the cover including a window such that indicia on the container are selectively visible through the window, and the toothbrush including corresponding indexing structures on the container and the cover, the indexing structures facing inwardly from an interior wall of the cover and the indexing structures facing outwardly from the container;

filling at least one of the plurality of compartments of the container with medication;

using the toothbrush in a regular dental hygiene routine; and taking the medication during the routine.

17. The method of claim 16, wherein the closure has an opening and is rotatably associated with the container and taking the medication during the routine comprises:

rotating the closure;

orienting the opening with one of the plurality of compartments filled with medication;

dispensing the medication from said compartment through the opening; and imbibing the medication.

\* \* \* \* \*